United States Patent
Thorne et al.

(10) Patent No.: US 8,808,313 B2
(45) Date of Patent: Aug. 19, 2014

(54) SUTURE PASSING AND RETRIEVAL DEVICE

(75) Inventors: Marc Thorne, Wakefield, RI (US);
Darren W. Thomsen, Largo, FL (US)

(73) Assignee: Linvatec Corporation, Largo, FL (US)

( * ) Notice: Subject to any disclaimer, the term of this patent is extended or adjusted under 35 U.S.C. 154(b) by 1183 days.

(21) Appl. No.: 11/827,515

(22) Filed: Jul. 12, 2007

(65) Prior Publication Data

US 2009/0018554 A1 Jan. 15, 2009

(51) Int. Cl.
*A61B 17/04* (2006.01)
*A61B 17/12* (2006.01)

(52) U.S. Cl.
CPC ......... *A61B 17/0485* (2013.01); *A61B 17/0469* (2013.01)
USPC .......................................... 606/145

(58) Field of Classification Search
USPC .................. 606/113, 144–150, 205, 211, 224
See application file for complete search history.

(56) References Cited

U.S. PATENT DOCUMENTS

| | | | |
|---|---|---|---|
| 3,791,387 A | 2/1974 | Itoh | |
| 3,877,434 A | 4/1975 | Ferguson et al. | |
| 5,201,741 A | 4/1993 | Dulebohn | |
| 5,234,445 A | 8/1993 | Walker et al. | |
| 5,336,231 A * | 8/1994 | Adair | 606/148 |
| 5,573,542 A * | 11/1996 | Stevens | 606/144 |
| 5,906,626 A * | 5/1999 | Carrillo | 606/148 |
| 6,966,914 B2 | 11/2005 | Abe | |
| 7,156,857 B2 * | 1/2007 | Pasricha et al. | 606/148 |
| 7,918,868 B2 * | 4/2011 | Marshall et al. | 606/144 |
| 2002/0147456 A1 * | 10/2002 | Diduch et al. | 606/144 |
| 2005/0121042 A1 * | 6/2005 | Belhe et al. | 128/887 |

* cited by examiner

*Primary Examiner* — Melanie Tyson (57) ABSTRACT

A surgical instrument has a suture passer/advancer and a suture retriever manipulated from a common handle. The retriever is preferably a loop that closes around the suture advanced through it by the advancer. The loop is retracted to draw it around the suture. The passer/advancer has a fork-like distal end to readily advance and let go of the suture after it is in the loop of the retriever. The advancer and retriever can be manipulated longitudinally and rotationally with respect to a tubular body through which they extend so that the suture retriever can be passed through a needle pierced through tissue to be sutured, and the suture may be advanced and guided into the retriever loop to be gripped. Retracting the instrument will cause one end of the suture to be pulled retrograde through the tissue.

8 Claims, 7 Drawing Sheets

SUTURE PASSING AND RETRIEVAL DEVICE

FIELD OF THE INVENTION

The field of the invention is surgical instruments and more particularly instruments used to advance and retain a suture through tissue.

BACKGROUND OF THE INVENTION

Suture is commonly used during open and closed (endoscopic) surgery. One of the more challenging aspects of using suture is passing the suture through tissue to be sutured and retrieving the suture so that it can be tied to a selected location, to a suture anchor or otherwise manipulated to treat the target tissue.

Suture hooks are cannulated needles which are able to be pierced through tissue. One end of a length of suture may be passed through the lumen of the cannulated needle in antegrade fashion in order to pass the suture from a point exterior to the surgical work site and through the tissue to be sutured. The needle can then be removed and a suture snare, grasper or similar device may then be used to engage the end of suture passing through the tissue and position it also at an accessible point away from the work site near the other end of the suture. The two suture ends may then be tied or otherwise manipulated to treat the tissue. Such devices are commonly used during arthroscopic surgical procedures. The use of such known surgical instruments is complicated by the fact that they must be sequentially used thereby requiring extra steps and additional time which increases the overall complexity and duration of the surgical procedure. Other art in the field of the present invention is illustrated in U.S. Pat. No. 6,966,914 (Abe); U.S. Pat. No. 5,234,445 (Walker et al.); U.S. Pat. No. 3,877,434 (Ferguson et al.); U.S. Pat. No. 5,201,741 (Dulebohn) and U.S. Pat. No. 3,791,387 (Itoh).

Accordingly, it is an object of the present invention to produce a surgical instrument which combines the suture passing and suture retrieving functions.

SUMMARY OF THE INVENTION

A surgical instrument has a suture passer and a suture retainer manipulated from a common handle. The retainer is preferably a loop that closes around the suture advanced through it by the advancer. The loop is retracted to draw it around the suture. The retainer has a fork like distal end to readily advance and let go of the suture after it is in the loop of the retainer. The advancer and retainer can be manipulated longitudinally and rotationally with respect to a tubular body through which they extend so that the advanced suture can be guided into the loop to be gripped.

DETAILED DESCRIPTION OF THE PREFERRED EMBODIMENT

Figure 1:
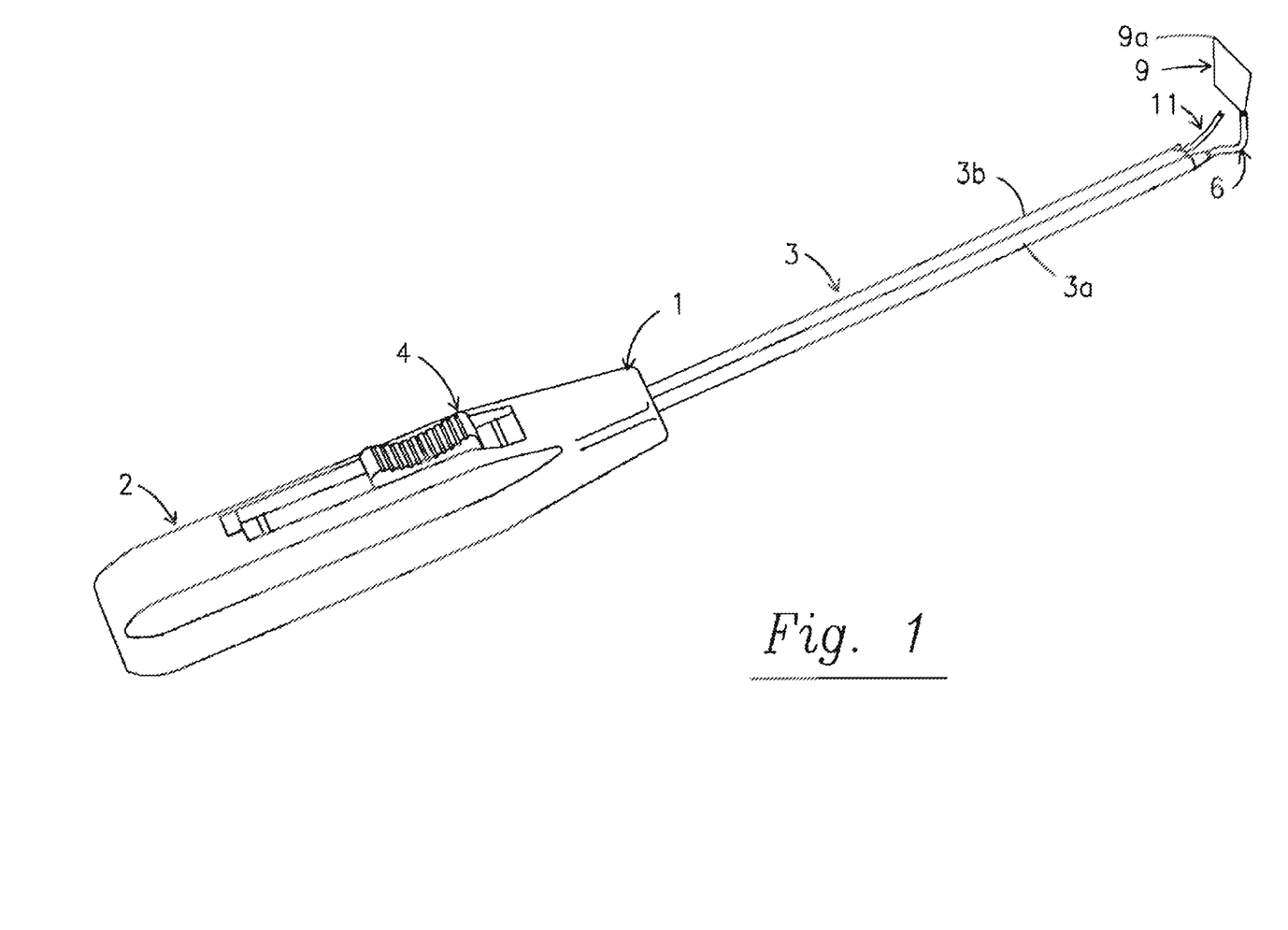
FIG. 1 shows a perspective view of a suture passer/retriever instrument constructed in accordance with the principles of this invention showing components extending from the distal tip of the instrument.

FIG. 1 shows a preferred embodiment of a suture passer/retriever instrument 1 constructed in accordance with the principles of this invention. Instrument 1 comprises a handle 2 having a dual lumen tubular member extending from its distal end. Handle 2 further comprises a first thumb/finger actuator or slide 4 and a second thumb/finger actuator or slide (not shown) for controlling movement of other components of instrument 1 as will be understood below.

Tubular member 3 in the preferred embodiment comprises a first cylindrical tube 3a and a second cylindrical tube 3b, both tubes being joined together in parallel alignment. Alternatively, tubular member 3 could be a single cylindrical or tubular tube containing two parallel lumens within its interior.

Tubular member 3a is provided at its distal end with a curved cannulated needle tip 6 aligned with the lumen of tube 3a. It will be understood that the size of the tubular member 3 and the curvature of needle tip 6 is small enough to enable the distal end of instrument 1 to pass through a cannula or portal used to access the surgical work site during arthroscopic or other endoscopic procedures. The needle tip 6 has a sharpened distal end adapted to pierce tissue to be sutured. Tubular member 3a and needle tip 6 are adapted to slidably receive a suture retrieving member 9 which comprises a distal loop 9a and a body portion (not shown) attaching the loop to thumb/finger actuator 4. It will be understood that FIG. 1 shows retrieving member 9 extended somewhat. When actuator 4 is in its proximal-most position loop 9a will normally be fully retracted into the lumen within tubular member 3a. In this position, needle tip 6 may pierce tissue without interference from loop 9a.

Tubular member 3b is adapted to slidably receive a suture advancer or push rod 11 which is provided at its distal tip with a suture retainer which in the preferred embodiment is in the form of a U-shaped clip 8 which may be further in the form of a narrowed slot adapted to frictionally engage suture 12. The push rod 11 may be in any suitable form such as, for example, a flat ribbon, a tubular shaft, a solid rod of predetermined cross-section, etc. Push rod 11 is connected at its proximal end to the second thumb/finger actuator which is slidable between a proximal-most position in which push rod 11 and clip 8 are retracted entirely within the lumen of tubular member 3b and a distal-most position in which push rod 11 is extended from the lumen as will be understood below. It will be understood that the configuration of instrument 1 prior to its actual use in a surgical procedure would include both thumb/finger actuators preferably being retracted entirely within their respective lumens.

Figure 2:
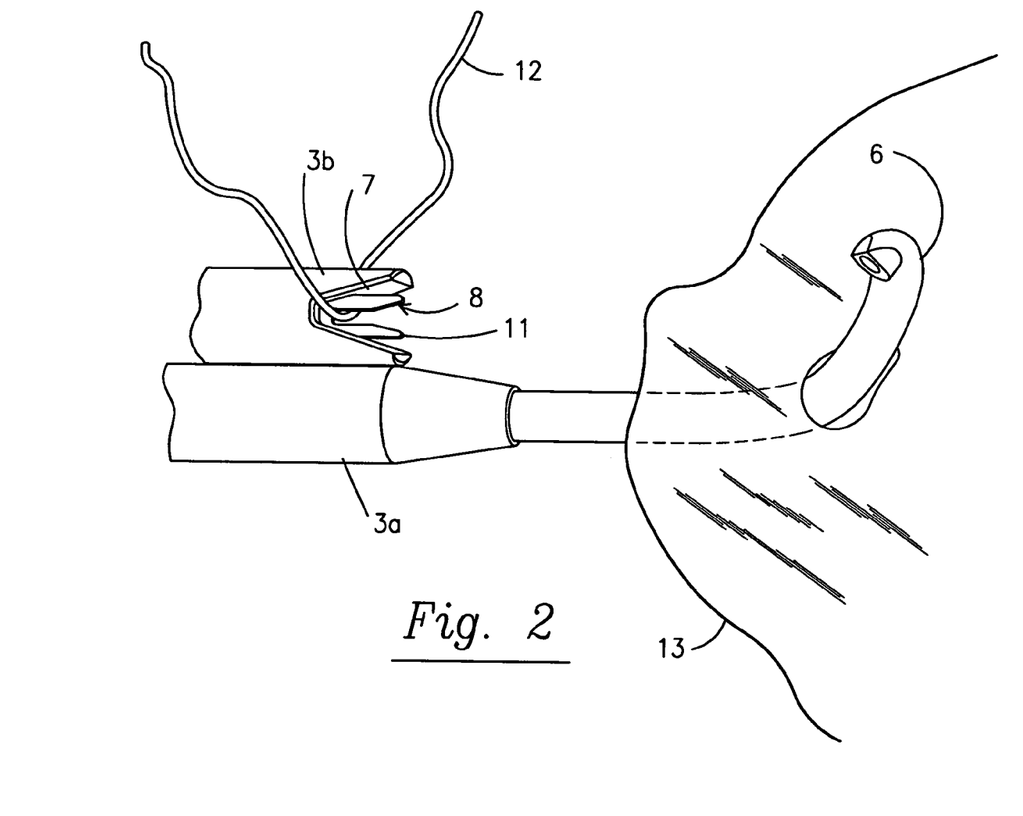
FIG. 2 shows a view of the distal end of the instrument of FIG. 1 after it has penetrated through tissue to be sutured.

The operation of the invention will best be understood by reference to FIGS. 2 through 7. As shown in FIG. 2, needle tip 6 is pierced through tissue 13 at a location where the surgeon desires to pass suture. At this stage, push rod 11 is retracted within the lumen of tubular member 3b and suture 12 is engaged within suture clip 8. It will be understood that suture clip 8 may engage a length of suture at any point intermediate the ends of the suture to be passed. Preferably clip 8 engages suture near one of the ends of the suture as will be understood below. The portions of suture 12 are guided proximally from clip 8 either within the lumen of tubular member 3b or along the exterior of tubular member 3 in order to avoid becoming tangled and/or interfering with the surgical procedure. The distal end of tubular member 3b is provided with a notch 7 to accommodate the suture.

Figure 3:
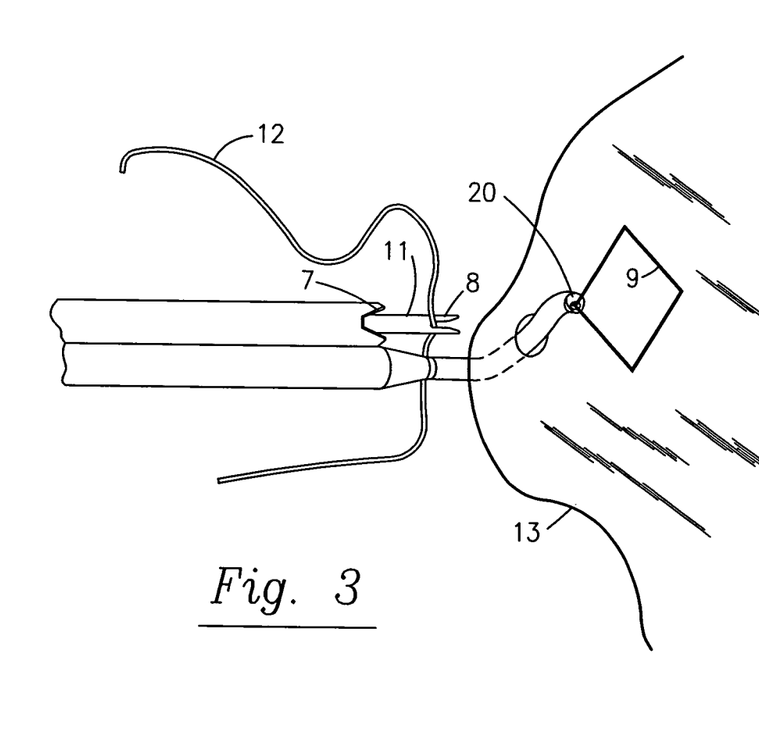
FIG. 3 is a view of the distal end of the instrument of FIG. 1 showing the configuration of components during use of the instrument.

As shown in FIG. 3, once the needle tip 6 has pierced tissue 13, the opening 20 of the needle will be exposed above the surface of the tissue and actuator 4 may then be pushed distally in order to advance suture loop 9a along one predetermined path so that it can automatically open up when unrestrained by the lumen of needle 6. It will be understood that suture retriever loop 9a may be made of a shape-memory material such as Nitinol so that it will adopt a preformed shape once it is released from the needle. In the preferred embodiment loop 9a is preformed into the shape of a diamond although it will be understood that a variety of shapes would be suitable provided the loop can be collapsed onto the suture and into the lumen of the needle.

Figure 4:
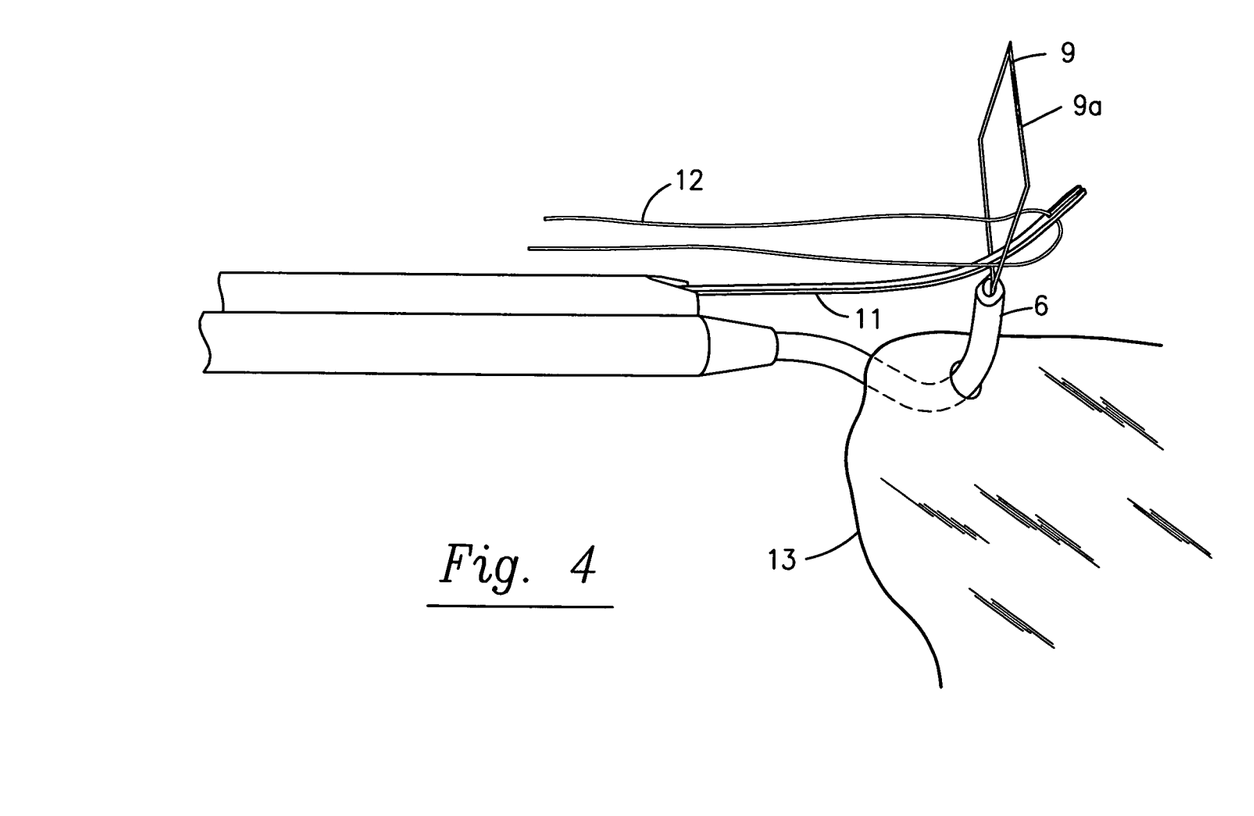
FIG. 4 is another view of the distal end of the instrument showing the configuration of components during use of the instrument.

When loop 9a is satisfactorily positioned above tissue 13, push rod 11 is pushed distally by distal motion of the second actuator. Referring now to FIG. 4, it will be understood that further distal extension of push rod 11 causes it to extend along another predetermined path into the path of suture retrieving member 9 and through loop 9a. Push rod 11 is formed of a shape retaining material such as Nitinol so that its distal end will automatically curve as required (as it exits the lumen) to follow a path designed to intersect the path of suture retrieving member 9 and to place the suture through loop 9a.

Figure 5:
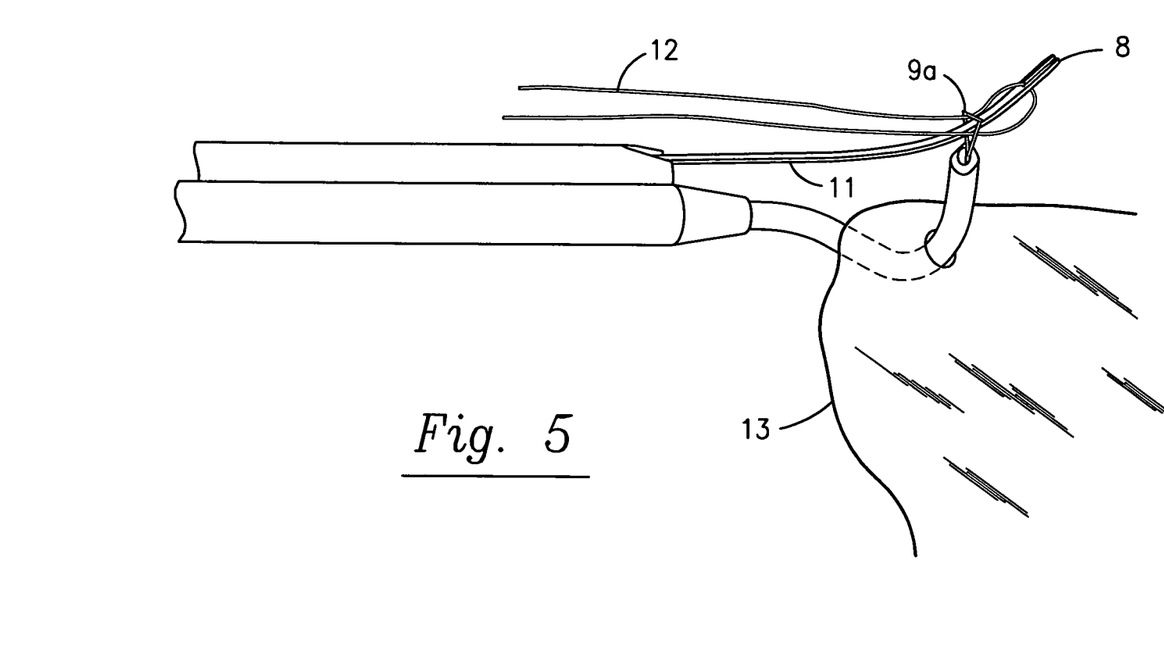
FIGS. 5 through 7 are views showing various configurations of the components of the instrument during other stages of the method of using the instrument.

As shown in FIG. 5, once push rod 11 has been advanced sufficiently to position suture clip 8 distally of loop 9a, suture retrieving member 9 can be retracted by the proximal motion of actuator 4 so that loop 9a can, as it is compressed by the lumen of the needle tip, collapse around suture 12 and push rod 11.

Figure 6:
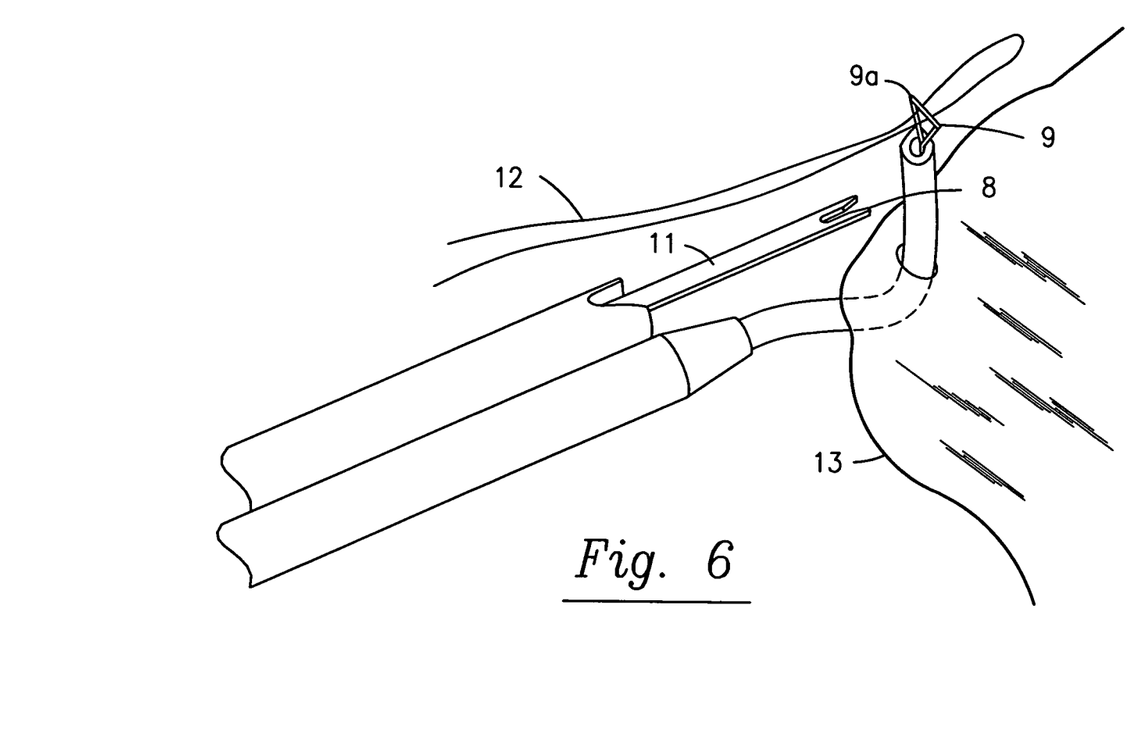
Figure 7:
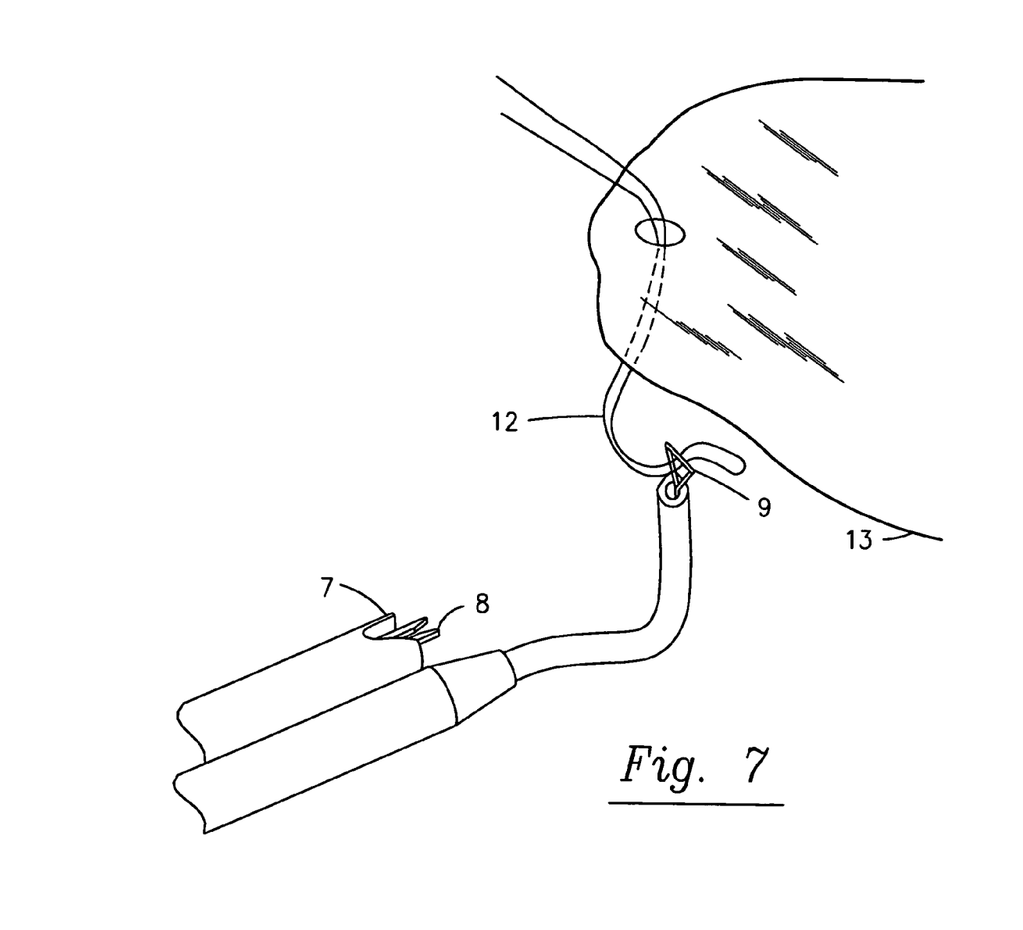

As shown in FIG. 6, once loop 9a has been collapsed around suture 12, push rod 11 may be retracted by the proximal motion of the second actuator in order to disengage clip 8 from suture 12, allowing only the suture to remain within loop 9a. Suture retrieving member 9 is retracted sufficiently to enable it to securely retain suture 12 while needle tip 6 is retracted from tissue 13 as shown in FIG. 7 to pull the suture through the tissue in retrograde fashion. Instrument 1 may then be removed from the work site thereby pulling one or both ends of suture 12 through tissue 13 as far as desired by the surgeon. Preferably, only one end of suture 12 would then be completely pulled through the tissue thereby enabling tissue 13 to be tied to a desired location in a conventional manner.

While shown in a straight configuration, it will be understood that tubular members 3a and 3b could be curved to facilitate access to certain work sites. The body portions of push rod 11 and suture retriever 9 are flexible enough to curve within the lumens of the tubular members and needle tip 6, which itself can be shaped into a variety of curvatures of varying degrees.

It will be understood by those skilled in the art that numerous improvements and modifications may be made to the preferred embodiment of the invention disclosed herein without departing from the spirit and scope thereof.

What is claimed is:

1. A surgical instrument for manipulating a suture comprising:
    an elongated body comprising two parallel lumens;
    a suture advancer movably mounted within a second of said lumens, said suture advancer being a flat ribbon comprising a distal facing u-shaped slot;
    a suture retriever movably mounted within a first of said lumens, said suture retriever comprising a distal loop made of a shape-memory material such that in a released state said distal loop will adopt a preformed shape; and
    a curved cannulated needle tip provided at a distal end of said body such that a lumen of the cannulated needle is an extension of and in alignment with said first lumen, said cannulated needle comprising a sharpened distal end adapted to pierce tissue to be sutured, said curved cannulated needle tip being positioned at a location distal to a distal end of said second lumen,
    wherein at least a portion of said suture retriever is movable between a retracted state within said cannulated needle tip and said released state beyond said cannulated needle, and
    wherein a path of said suture advancer selectively intersects with said suture retriever in said released state.

2. The instrument of claim 1 wherein:
    said suture advancer is movable longitudinally or rotationally with respect to said body for selective entry into said loop.

3. The instrument of claim 2 wherein:
    said suture advancer is movable longitudinally and rotationally with respect to said body for selective entry into said loop.

4. The instrument of claim 3 wherein:
    said body comprises two tubes being joined together in parallel alignment.

5. The instrument of claim 4 wherein:
    said body further comprises a handle on a proximal end thereof through which said suture advancer and said suture retriever can be manipulated with respect to a distal end of said body.

6. A suture passer comprising:
    a tubular member having a first lumen and a second lumen, portion of said second lumen being joined to said first lumen in a parallel alignment, said first lumen having proximal and distal ends and said second lumen having proximal and distal ends, said distal end of said first lumen being provided with a curved cannulated needle tip being positioned at a location distal to said distal end of said second lumen, said curved cannulated needle tip comprising a sharpened distal end adapted to pierce tissue to be sutured;
    a first member having a proximal end and distal collapsible loop, said first member slidably situated within said first lumen, said first member adapted to be controlled from its proximal end to enable said collapsible loop to extend from said first lumen along a first predetermined path, said collapsible loop being made of a shape-memory such that in a released state said collapsible loop will adopt a preformed shape;
    a second member having a proximal and distal end, said second member being a flat ribbon having a distal facing, u-shaped suture engaging means at its distal end and slidably situated within said second lumen, said second member adapted to be controlled from its proximal end to extend from said second lumen along a predetermined path which intersects said first predetermined path to enable its distal end to extend through said collapsible loop; and
    a suture having a portion releasably engaged by said suture engaging means whereby, when said first member is deployed from said first lumen and said second member is deployed from said second lumen and said first member is retracted into said first lumen, said suture will be grasped within said collapsible loop.

7. A suture passer according to claim 6 further comprising:
a first actuating means attached to the proximal end of said first member for slidably moving said first member relative to said first lumen;
a second actuating means attached to the proximal end of said second member for slidably moving said second member relative to said second lumen.

8. A suture passer comprising:
a tubular member having a first lumen and a second lumen, a portion of said second lumen being joined in parallel alignment to said first lumen, each of said first and second lumens having proximal and distal ends, said distal end of said first lumen being provided with a curved cannulated needle comprising a sharpened distal end adapted to pierce tissue to be sutured, said curved cannulated needle tip being positioned at a location distal to a distal end of said second lumen;
a suture to be placed at a surgical site;
a suture advancing member being a flat ribbon having a distal facing u-shaped slot for advancing a portion of said suture, the suture advancing member being slidably retained within said second lumen and extendable distally beyond said distal end of said second lumen along a projected/predetermined path;
a suture retrieving member slidably retained within said first lumen, said suture retrieving member having a looped distal end adapted to extend from said distal end of said first lumen and to intersect said predetermined path of said suture advancing member, said looped distal end being made of a shape-memory material such that in a released state the looped distal end will adopt a preformed shape;
means for retracting said suture retrieving member to engage said suture advancing member and suture;
means for retracting said suture advancing member from engagement with said suture retrieving member while leaving said suture engaged with said suture retrieving member.

* * * * *